(12) United States Patent
Reutter et al.

(10) Patent No.: US 10,330,133 B2
(45) Date of Patent: Jun. 25, 2019

(54) ADAPTER FOR RECEIVING A MEDICAL TECHNICAL DEVICE AND A POSITION DETECTING SYSTEM

(71) Applicant: Scopis GmbH, Berlin (DE)

(72) Inventors: Andreas Reutter, Berlin (DE); Christopher Oezbek, Berlin (DE); Bartosz Kosmecki, Berlin (DE)

(73) Assignee: Scopis GmbH, Berlin (DE)

( * ) Notice: Subject to any disclaimer, the term of this patent is extended or adjusted under 35 U.S.C. 154(b) by 801 days.

(21) Appl. No.: 14/967,753

(22) Filed: Dec. 14, 2015

(65) Prior Publication Data

US 2017/0167514 A1    Jun. 15, 2017

Related U.S. Application Data

(63) Continuation-in-part of application No. PCT/EP2014/062424, filed on Jun. 13, 2014.

(30) Foreign Application Priority Data

Jun. 13, 2013 (DE) .................. 10 2013 211 055

(51) Int. Cl.
*F16B 2/12* (2006.01)
*A61B 90/00* (2016.01)
(Continued)

(52) U.S. Cl.
CPC ................ *F16B 2/12* (2013.01); *A61B 90/39* (2016.02); *A61B 2017/00477* (2013.01); *A61B 2034/2055* (2016.02); *A61B 2090/3983* (2016.02)

(58) Field of Classification Search
CPC ... F16B 2/12; F16B 2/06; A61B 17/02; F16G 11/10; F16M 11/04; F16M 11/041; F16M 11/048
See application file for complete search history.

(56) References Cited

U.S. PATENT DOCUMENTS 3,581,354 A    6/1971    Usiskin
4,867,404 A    9/1989    Harrington
(Continued)

FOREIGN PATENT DOCUMENTS

DE    20 2006 019649 U1    8/2007

OTHER PUBLICATIONS

Baumhauer, M. et al., "Navigation in Endoscopic Soft Tissue Surgery—Perspectives and Limitations", Journal of Endourology, vol. 27, Issue 4, Apr. 17, 2008, pp. 1-15.
(Continued)

*Primary Examiner* — Daniel J Wiley
(74) *Attorney, Agent, or Firm* — Howard & Howard Attorneys PLLC

(57) ABSTRACT

An adapter for receiving a medical technical device and a position detecting system, wherein the adapter may comprise a first holding element, a second holding element, a spring exerting a restoring force on the second holding element, and a fixing element for fixing the position detecting system. The second holding element may be supported by the first holding element such that it can move and can be moved in a direction counter to the restoring force of the spring placing the adapter in a receiving state allowing the medical technical device to be inserted into the adapter. In the absence of the force acting counter to the restoring force of the spring, the spring may move the second holding element in the direction of the restoring force, placing the adapter in a clamping state and securing the adapter to the medical technical device.

14 Claims, 8 Drawing Sheets

(51) Int. Cl.
*A61B 34/20* (2016.01)
*A61B 17/00* (2006.01)

(56) References Cited

U.S. PATENT DOCUMENTS

| | | |
|---|---|---|
| 6,190,395 B1 | 2/2001 | Williams |
| 6,301,495 B1 | 10/2001 | Gueziec et al. |
| 6,466,815 B1 | 10/2002 | Saito et al. |
| 6,850,794 B2 | 2/2005 | Shahidi |
| 7,379,077 B2 | 5/2008 | Bani-Hashemi et al. |
| 7,605,826 B2 | 10/2009 | Sauer |
| 7,844,320 B2 | 11/2010 | Shahidi |
| 7,993,353 B2 | 8/2011 | Roeβner et al. |
| 7,995,076 B2 | 8/2011 | Emam et al. |
| 8,126,223 B2 | 2/2012 | Coste-Maniere et al. |
| 9,641,808 B2 | 5/2017 | Rose et al. |
| 9,646,423 B1 | 5/2017 | Sun et al. |
| 2005/0041966 A1 | 2/2005 | Johnson |
| 2008/0071142 A1 | 3/2008 | Gattani et al. |
| 2009/0321599 A1 | 12/2009 | Huang |
| 2010/0295931 A1 | 11/2010 | Schmidt |
| 2012/0280988 A1 | 11/2012 | Lampotang et al. |
| 2013/0245460 A1 | 9/2013 | King et al. |
| 2014/0193056 A1 | 7/2014 | Neff |
| 2014/0275975 A1 | 9/2014 | Coste-Maniere et al. |
| 2014/0330115 A1 | 11/2014 | Schildkraut et al. |
| 2016/0008083 A1 | 1/2016 | Kesten et al. |
| 2016/0120609 A1 | 5/2016 | Jacobsen et al. |
| 2016/0270863 A1 | 9/2016 | Makower |
| 2016/0360117 A1 | 12/2016 | Elefteriu et al. |
| 2017/0007350 A1 | 1/2017 | Popovic et al. |

OTHER PUBLICATIONS

Caversaccio, M.D., Marco et al., "Computer-Assistance for Intraoperative Navigation in ENT Surgery", Minimally Invasive Therapy & Allied Technologies, vol. 12, Issue 1-2, 2003, pp. 1-40.

Freysinger, W. et al., "Image-Guided Endoscopic ENT Surgery", Eur Arch Otorhinolaryngol, vol. 254, 1997, pp. 343-346.

Wormald, Peter-John, "Surgery for the Frontal Recess and Frontal Sinus", Rhinology, vol. 43, 2005, pp. 82-85.

ADAPTER FOR RECEIVING A MEDICAL TECHNICAL DEVICE AND A POSITION DETECTING SYSTEM

CROSS-REFERENCE TO RELATED APPLICATIONS

The present application is a continuation-in-part of PCT Application No. PCT/EP2014/062424 filed on Jun. 13, 2014 and published as WO 2014/198922 claiming priority of German Patent Application No. DE 10 2013 211 055.3 filed on Jun. 13, 2013. The aforementioned applications are hereby incorporated by reference in its entirety.

BACKGROUND OF THE INVENTION

Field of the Invention

This invention relates to an adapter for receiving a medical technical device as well as a position detecting system.

Brief Description of the Related Art

In medical technology, clinical navigation systems are known, with the help of which, e.g. during an operation, the spatial position of an instrument (e.g. an endoscope) can be determined, in order to enable their display in the correct position in imaging representations (e. g. in the form of a CT image) of an operating field. The display in the correct position requires a transformation of the spatial position, determined by the position detecting system, of the instrument into the coordinate system of the representation of the operating field. Especially optical measuring systems are used as position detecting systems, which by means of several cameras sense the position of trackers, which consist of several fixedly connected, predominantly spherically shaped marker elements. Alternatively, also electromagnetic measuring systems are employed, in the case of which the position of sensor coils is measured in an electromagnetic field generated by a field generator.

SUMMARY OF THE INVENTION

It is therefore an object of the present invention to provide an adapter for receiving a medical technical device as well as a position detecting system or a component of a position detecting system, enabling in a simple fashion to provide a connection between a position detecting system and a medical technical device, and allowing for a variable setting and combinability of the medical technical devices with a position detecting system of a clinical navigation system.

Provided is an adapter for receiving a medical technical device and a position detecting system, the adapter having a first holding element, a second holding element, a spring exerting a restoring force on the second holding element, and a fixing element for fixing the position detecting system, wherein the first holding element has a receiving opening with a longitudinal extension direction, the receiving opening being configured to receive the second holding element within the first holding element, and the longitudinal extension direction of the receiving opening of the first holding element being parallel to the direction of the restoring force of the spring, characterized in that the second holding element is movably supported in the first holding element and, by means of a force acting counter to the restoring force of the spring, is moveable in a direction counter to the restoring force of the spring such that the adapter is in a receiving state and the medical technical device is insertable into the adapter, wherein, in the absence of the force acting counter to the restoring force of the spring, the second holding element performs a movement in the direction of the restoring force by means of the restoring force of the spring and, as a result, the adapter is in a clamping state, in which the medical technical device inserted into the adapter is clamped between the first holding element and the second holding element.

It is intended that the first holding element has a first insertion opening for inserting the medical technical device, and the second holding element has a second insertion opening for inserting the medical technical device, the first insertion opening and the second insertion opening being configured to be transverse to the restoring force of the spring, and the first insertion opening and the second insertion opening completely passing through the first holding element and the second holding element, respectively, wherein the first insertion opening and the second insertion opening can be brought into coincidence by a force acting counter to the restoring force of the spring and the receiving state of the adapter is attained, and wherein, in the absence of the action of the force, the adapter, by to the restoring force of the spring, is in the clamping state.

It is further envisaged that the first holding element may have a first clamping element, and the second holding element may have a second clamping element, the second holding element, by a force acting counter the restoring force of the spring, being moveable such that the distance between the first clamping element and the second clamping element increases and the adapter is in the receiving state, wherein in the absence of the action of the force the adapter, by to the restoring force of the spring, is in the clamping state.

Further, the clamping state of the adapter may be reversible by a force acting against the restoring force of the spring and the medical technical device is removable from the adapter in this state.

It is further intended that a first displacing element, disposed at the second holding element, may have a thread on an outer face and is operatively connected to a second displacing element, having a receiving opening with a mating thread for receiving the first displacing element, such that, by a rotational movement of the second displacing element in a clamping direction, the first displacing element and, therefore, the second displacing element are moveable in the direction of the restoring force of the spring, and, thereby, the adapter is in a movement proof clamping state.

The movement proof clamping state of the adapter may be reversible by a rotational movement of the second displacing element counter to the clamping direction.

The adapter according to any one of the preceding claims, characterized in that the fixing element is immobilized on the second holding element, and the position detecting system has a fixing counter-element that is capable of engaging with the fixing element.

The fixing element may have a cavity with a thread, and the fixing counter-element may have a receiving opening with an identical thread, the cavity of the fixing element and the receiving opening of the fixing counter-element being directed in the direction of the restoring force of the spring and being configured such that, by means a screw and a nut, a locking state of the position detecting system with the adapter being attainable by a force-fitting connection of the fixing element, the fixing counter-element, the screw, and the nut by means of a rotational movement of the nut in a locking direction.

The fixing element and fixing counter-element may have on their mutual contact surfaces structures engaging with one another, and especially tooth structures engaging with one another, such that in the locking state a form-fitting and force-fitting locking of the position detecting system with the adapter being attained.

It is intended that in a non-locking state the position detecting system is rotatably supported, and, as a result, the spatial orientation of the position detecting system may be settable.

The spatial disposition of the position detecting system may be settable in an angle determined by the size of the structure elements of the fixing element and the fixing counter-element.

The spring may be connected to a bottom side of the second holding element.

BRIEF DESCRIPTION OF THE FIGURES

For a more complete understanding of the instant invention and the advantages thereof, reference is now made to the following description and the accompanying drawing, in which.

DETAILED DESCRIPTION OF THE INVENTION

Figure 1:
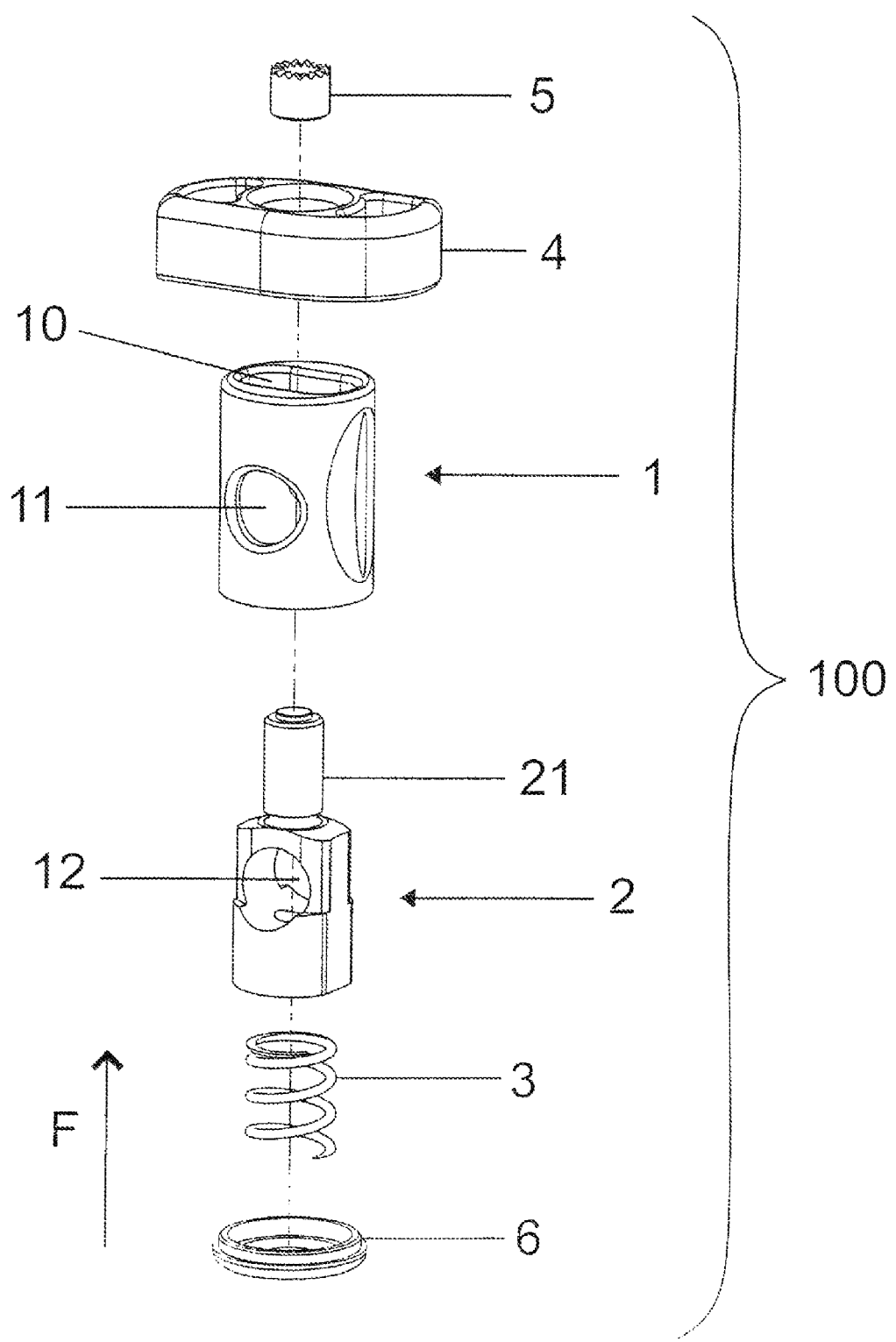
FIG. 1 shows an exploded view of an embodiment of the adapter according to the invention for receiving a medical technical device and a position detecting system.

The invention will now be described in detail. Drawings and examples are provided for better illustration of the invention. It will be understood that the embodiments and aspects of the invention described herein are only examples and do not limit the protector's scope of the claims in any way. The invention is defined by the claims and their equivalents. It will be understood that features of one aspect or embodiment of the invention can be combined with the feature of a different aspect or aspects and/or embodiments of the invention.

An adapter for receiving a medical technical device as well as a position detecting device is provided having a first holding element, a second holding element, a spring exerting a restoring force on the second holding element and, e. g., being configured to operatively connect to a lower side of the second holding element, as well as a fixing element for fixing the position detecting system.

Furthermore, the first holding element has a receiving opening with a longitudinal extension direction, which is configured to receive the second holding element within the first holding element, the longitudinal extension direction of the receiving opening being parallel to the direction of the restoring force of the spring.

According to the invention, the second holding element is moveably supported in the first holding element and, by a force acting counter to the restoring force of the spring in a direction opposite to the restoring force of the spring, is moveable in such a way that a receiving state of the adapter attained. In the receiving state, the medical technical device is insertable into the adapter.

In the absence of the force acting against the restoring force of the spring, the second holding element performs a movement in a direction of the restoring force by the restoring force of the spring. As a result, the adapter is in a clamping state, in which the medical technical device inserted into the adapter is clamped between the first holding element and the second holding element.

In one embodiment of the invention, the first holding element has a first insertion opening for inserting the medical technical device, and the second holding element has a second insertion opening for inserting the medical technical device, the first insertion opening and the second insertion opening being configured transverse to the restoring force of the spring, and the first insertion opening and the second insertion opening completely passing through the first holding element and the second holding element, respectively. Furthermore, the first insertion opening and the second insertion opening can be brought into congruence by a force acting against the restoring force of the spring, whereupon the receiving state of the adapter is attained. In the absence of the action of the force, the adapter, by the restoring force of the spring, is in the clamping state.

In a second embodiment, the first holding element has a first clamping element, and the second holding element has a second clamping element. The second holding element, by a force acting against the restoring force of the spring, is moveable such that the distance between the first clamping element and the second clamping element increases, and, as a result, the adapter is in the receiving state. In the absence of the action of the force, the adapter is in the clamping state by to the restoring force of the spring.

Furthermore, the clamping state of the adapter can, by a force acting against the restoring force of the spring, be suspended, and the medical technical device can subsequently be removed from the adapter in this state.

In a further embodiment, a first displacing element, disposed at the second holding element, has a thread on an outer face. The first displacing element is operatively connected to a second displacing element, having a receiving opening with a mating thread for receiving the first displacing element, such that, by a rotational movement of the second displacing element in a clamping direction (i.e. a direction of the second clamping element enabling a movement of the second holding element in the direction of the restoring force of the spring), the first displacing element and, therefore, the second displacing element are moveable in the direction of the restoring force of the spring. Thereby, the adapter is in a movement proof clamping state, i.e. the medical technical device is fixed at the adapter in a stationary manner.

Furthermore, the movement proof clamping state of the adapter may be suspended by a rotational movement of the second displacing element counter to the clamping direction.

In a further embodiment, the fixing element is immobilized on the second holding element, and the position detecting system has a fixing counter-element that is capable of engaging with the fixing element.

According to the invention, the fixing element may have a cavity with a thread, and the fixing counter-element may have a receiving opening with an identical thread, the cavity of the fixing element and the receiving opening of the fixing counter-element being directed in the direction of the restoring force of the spring. Furthermore, the fixing element and the fixing counter-element are configured such that, using a screw and a nut, a locking state of the position detecting system with the adapter may be attained by a force-fitting connection of the fixing element, the fixing counter-element, the screw, and the nut by means of a rotational movement of the nut in the locking direction.

Alternatively or additionally, the fixing element and fixing counter-element may have on their mutual contact surfaces structures engaging with one another, and especially tooth structures meshing with one another, such that in the locking state a form-fitting and force-fitting locking of the position detecting system with the adapter is attained.

In a further embodiment, the invention may provide that in a non-locking state the position detecting system is rotatably supported, as a result of which the spatial orientation of the position detecting system is settable. In particular, the spatial disposition may be set to predetermined angles determined by the size of the structure elements of the fixing element and fixing counter-element.

Moreover, the position detecting system may have three or more marker elements, which are fixedly connected to one another and to the fixing element. Alternatively, the position detecting system may consist of one or more sensor coils for electromagnetic position measuring with a fixedly connected fixing counter-element. The position detecting system may also be composed of a camera system of one or more cameras with a fixedly connected fixing counter-element.

The medical technical devices may be, e.g., surgical instruments such as a suction tube or a pointer for registering surface points.

The adapter according to the invention is preferably made of metal, especially of a titanium alloy. However, in the case of electromagnetic measurement methods, use of plastics is preferable.

The first embodiment of the adapter 100, shown in FIG. 1 in an exploded view, has a first holding element 1 having a receiving opening 10, which extends in a longitudinal extension direction, and an insertion opening 11. The receiving opening 10 extends completely through the first holding element 1 in a direction of the restoring force of the spring 3 and is configured such that a second holding element 2 may be accommodated in the first holding element 1.

Furthermore, the first insertion opening 11 of the first holding element 1 for insertion of a medical technical device (here not shown) is configured such that the insertion opening 11 extends transversely to the direction of the restoring force of the spring 3 through the entire first holding element 1.

Additionally, the adapter 100 has a second holding element 2 with a second insertion opening 12. The second insertion opening 12 is configured such that it extends completely through the second holding element 12 transversely to the direction of the restoring force of the spring 3. The spring 3 of the adapter 100 is disposed below the second holding element 2, the spring 3 being disposed such that it operatively connects with the lower side of the second holding element 2.

The first holding element 1 of the adapter 100 is immobilized at a bottom part 6 by, e.g., adhesive bonding or welding. The spring 3 is disposed within the first holding element 1. Furthermore the second holding element 2 is disposed above the spring 3 (and likewise within the first holding element 1), the second holding 2 element within the first holding element 1 being moveably disposed such that the second holding element 2, by a force acting counter to the direction of the restoring force of the spring 3—when the acting force is larger than the restoring force of the spring 3—, is moveable counter to the direction of the restoring force of the spring 3, or is, in the absence of a force acting on the spring 3, by the restoring force of the spring 3, moveable in a direction of the restoring force of the spring 3.

It is envisaged fore adapter 100 according to the invention, that the first insertion opening 11 and second insertion opening 12 of the first holding element 1 and the second holding element 2 may be brought into congruence by a force acting counter to the restoring force of the spring 3. By the action of such a force, the adapter 100 is, in the case of the first and second insertion openings 11 and 12 reaching coincidence, in a receiving state for a medical technical device. In this receiving state, the medical technical device may be inserted into the adapter 100 via the two insertions openings 11 and 12.

In the absence of the action of the force on the spring 3, the restoring force of the tensioned spring 3 causes a movement of the second holding element 2 in a direction of the restoring force of the spring 3. Thereby the clamping state of the adapter 100 is attained, in which a medical technical device inserted into the adapter 100 is clamped between the first holding element 1 and the second holding element 2.

The adapter 100 according to the invention furthermore has a first displacing element 21 provided with a thread and disposed on the second holding element 2, and a second displacing element 4 having a receiving opening with a mating thread. The second displacing element 4 is operatively connected to the first displacing element 21 such that in the case of a rotational movement in a locking direction (a rotational movement, in the case of which the second displacing element 4 moves in a direction counter to the restoring force of the spring 3) the first displacing element 21 and, therefore, the second displacing element 2 are moved in a direction of the restoring force of the spring 3. Thereby, a movement proof clamping state of the adapter 100 is attained, in which a medical technical device inserted into the adapter 100 is clamped between the first holding element 1 and the second holding element 2. A movement proof is to be understood such that the medical technical device is not further moveable in an insertion direction through the insertion openings 11 and 12, i.e., is connected to the adapter 100 in a stationary manner. Furthermore, the adapter 100 has an attachment element 5 for attachment of a position detecting system, which is immobilized at the upper side of the displacing element 21 by, e.g., welding or adhesive bonding. Regarding the mode of operation of the attachment element 5 for attachment of the position detecting system, reference is made to the descriptions of FIG. 5.

Figure 2:
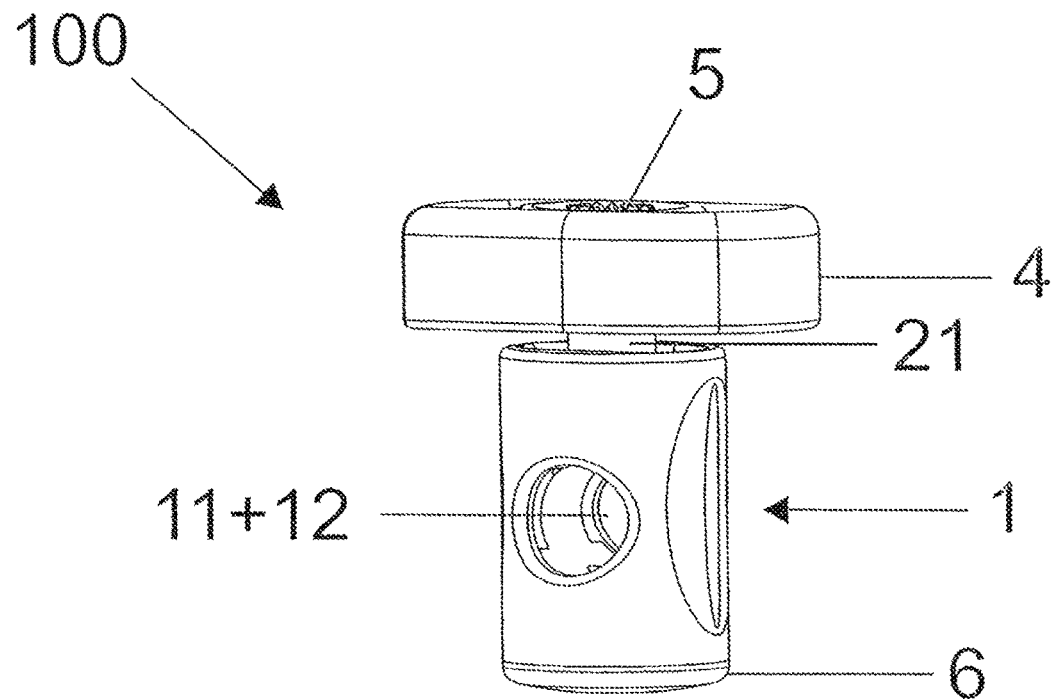
FIG. 2 shows the embodiment of FIG. 1 in a non-clamped state.

FIG. 2 shows the embodiment of FIG. 1 in a receiving state and, therefore, not in a clamped state. The second displacing element 4 thereby is an open state, and the two insertion openings 11 and 12 are brought into congruence by mechanical actions of forces (not shown here) such as compression. A medical technical device may at this stage be inserted through the two insertion openings 11 and 12 into the adapter 100.

Figure 3:
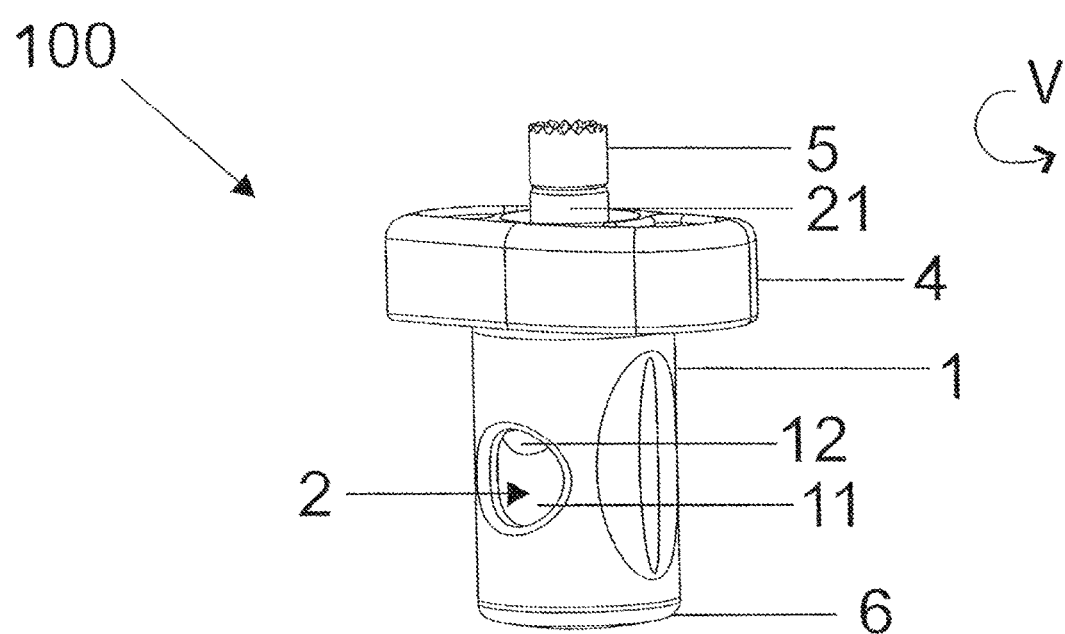
FIG. 3 shows the embodiment of FIG. 1 in a clamped state.

FIG. 3 shows the embodiment of FIG. 1 in a movement proof clamping state. The second displacing element 4 has thereby been rotated in a locking direction until reaching the movement proof clamping state. The second holding element 2 has thereby been moved in a direction of the restoring force of the spring 3. When reaching the movement proof clamping state shown in FIG. 3, a medical technical device, inserted into the adapter 100 in the receiving state of FIG. 2, is submitted to a movement proof clamping and thus remains stationary. For the sake of clarity, the medical technical device has been omitted from this figure.

The movement proof clamping state of the medical technical device is, in a manner analogous to what is shown FIG. 3, provided by a clamping of the medical technical device between the first holding element 1 and the second holding element 2 due to the movement of the second holding element 2 in a direction of the restoring force of the spring 3 by the rotational movement in a locking direction of the second displacing element 4.

Figure 4:
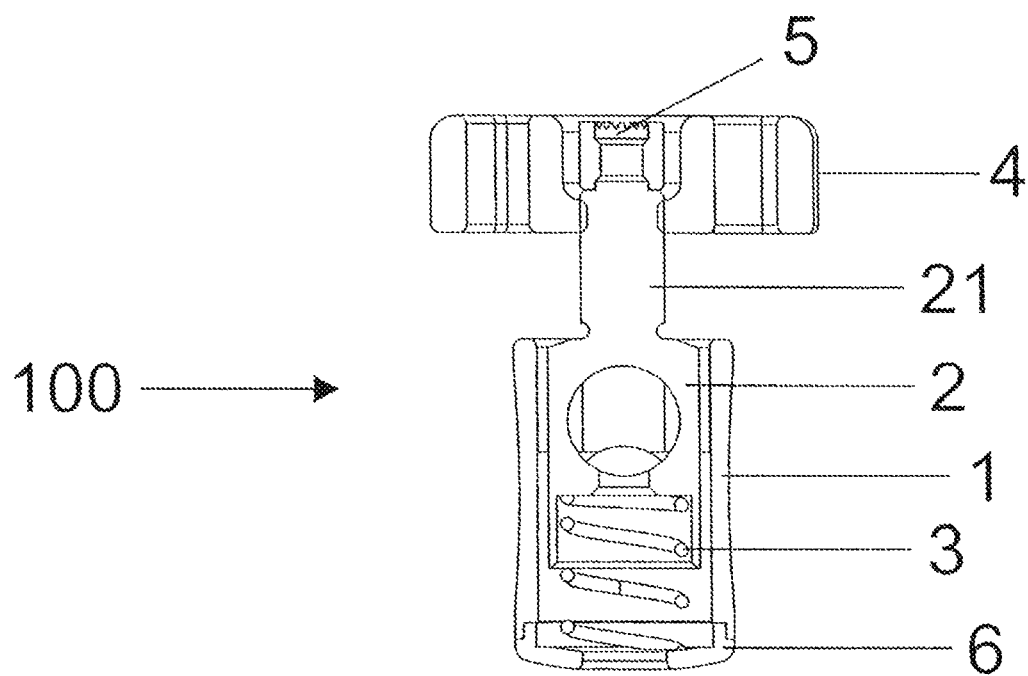
FIG. 4 shows a cross-section of the embodiment of FIG. 1 in a clamped state.

FIG. 4 shows a cross-sectional view of the first adapter according to the invention in a clamping state. The clamping state is in this case attained by the restoring force of the spring 3 moving the second holding element 2 in a direction of the restoring force of the spring 3. A clamping state is thereby attained by clamping of the medical technical device (not shown here for reason of clarity) between the first holding element 1 and the second element 2. By a rotational movement of the displacing element 4, then a movement proof clamping state may be attained in a manner analogous to the description of FIG. 3.

Figure 5:
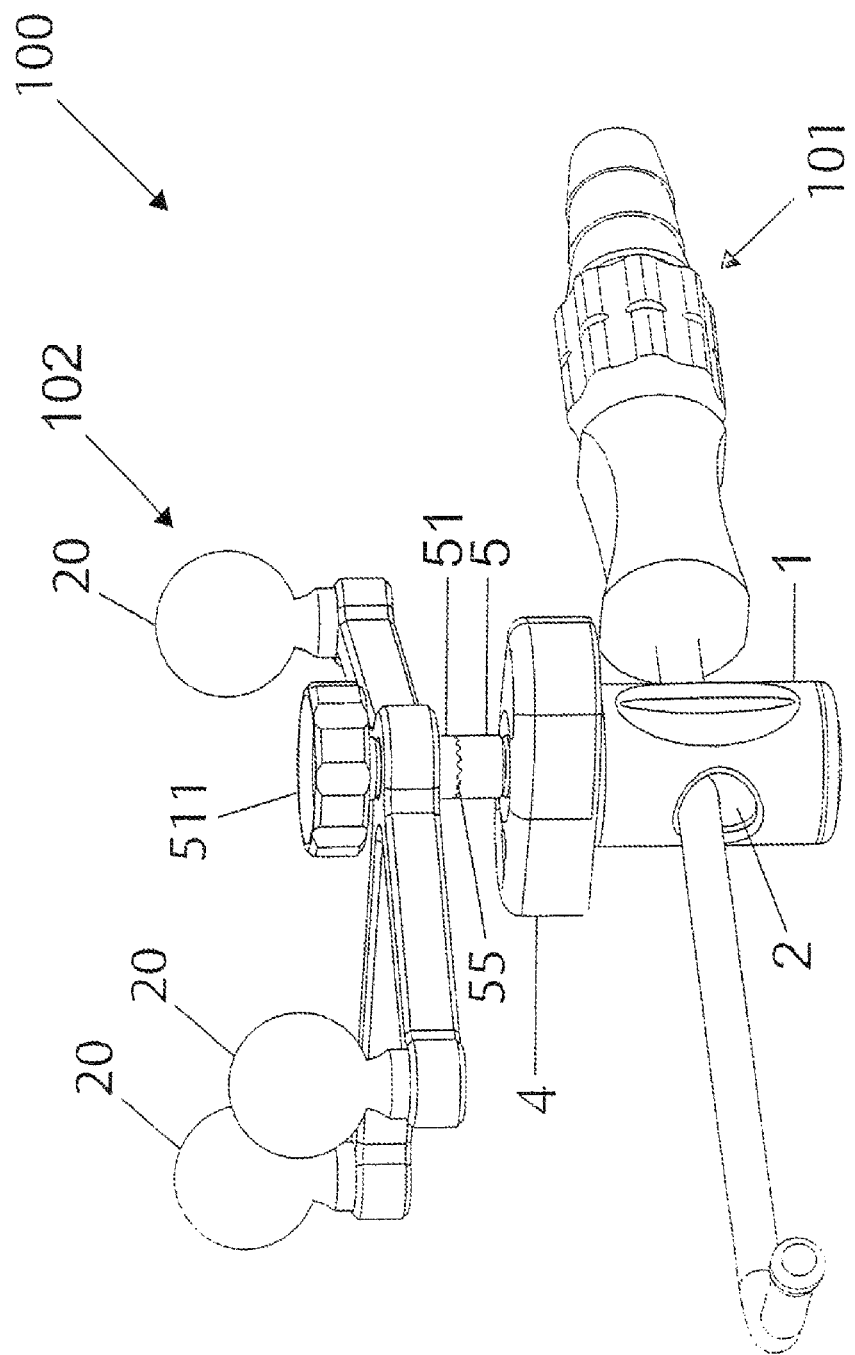
FIG. 5 shows the embodiment of FIG. 1 with a position detecting system in the form of a tracker with three marker elements for optical position measuring and with a suction tube in a clamped state.

FIG. 5 shows an adapter according to the invention with a medical technical device (in this case a suction tube) and a position detecting system in the form of a tracker for optical position measuring with three marker elements 20 in a clamping state. Regarding the clamping state of the medical technical device reference is made to the descriptions of FIG. 2 to FIG. 4.

The adapter according to the invention has an attachment element 5, and the position detecting system 102 has an attachment counter-element 51, which both have engaging structures 55 (in this case engaging teeth). A locking state of the position detecting system with the adapter according to the invention is thereby attained by cooperation of the attachment element 5, the attachment counter-element 51, the nut 511, and a screw not shown here.

The attachment element 5 thereby has a cavity with a thread, and the attachment counter-element 51 has a receiving opening with an identical thread. The attachment element 5 is connected to the attachment counter-element 51 by means of a screw fitted to the thread and is brought into a locking state by means of the nut 511 by a rotational movement in a locking direction. By engagement of the structured surfaces 55 at the mutual contact surfaces of the attachment element 5 and the attachment counter-element 51, a force-fitting and form-fitting connection is thereby attained.

Furthermore, in case of the adapter according to the invention, the position detecting system 102 is rotatably mounted. In case a complete locking state by a rotational movement of the nut 511 in an end position of the locking direction has not been attained, the spatial disposition of the position detecting system may be variably set, wherein the settable angles are predetermined by the mutually engaging structure elements 55 of the attachment element 5 and the attachment counter-element 51.

Figure 6:
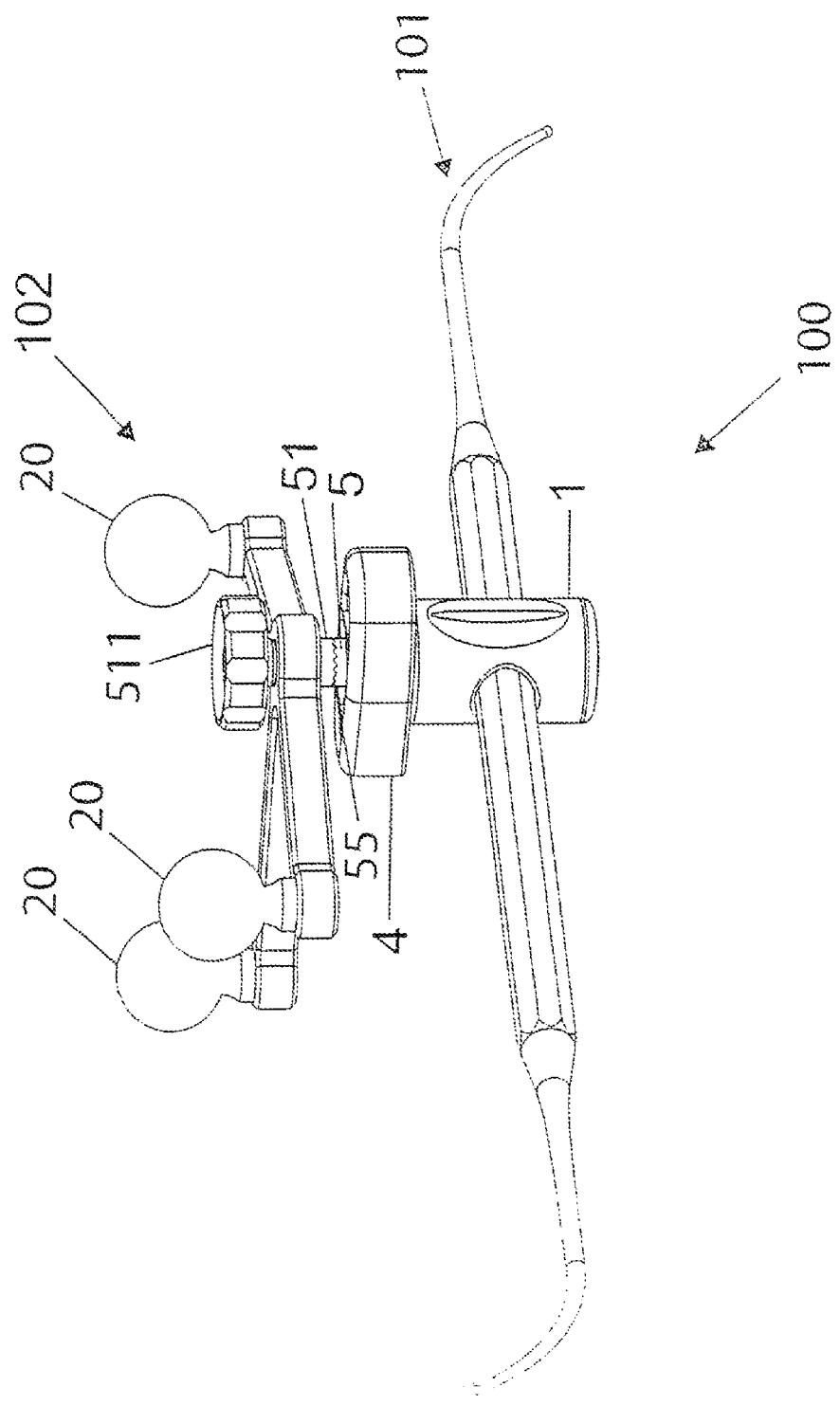
FIG. 6 shows the embodiment of FIG. 1 with a position detecting system in the form of a tracker with three marker elements for optical position measuring and with a pointer for registering surface points.

FIG. 6 shows an adapter according to the invention in a first embodiment with a medical technical device (in this case a pointer) and a position detecting system in the form of a tracker with three marker elements in a clamping state. Regarding the further descriptions reference is made to FIG. 2 to FIG. 5.

Figure 7:
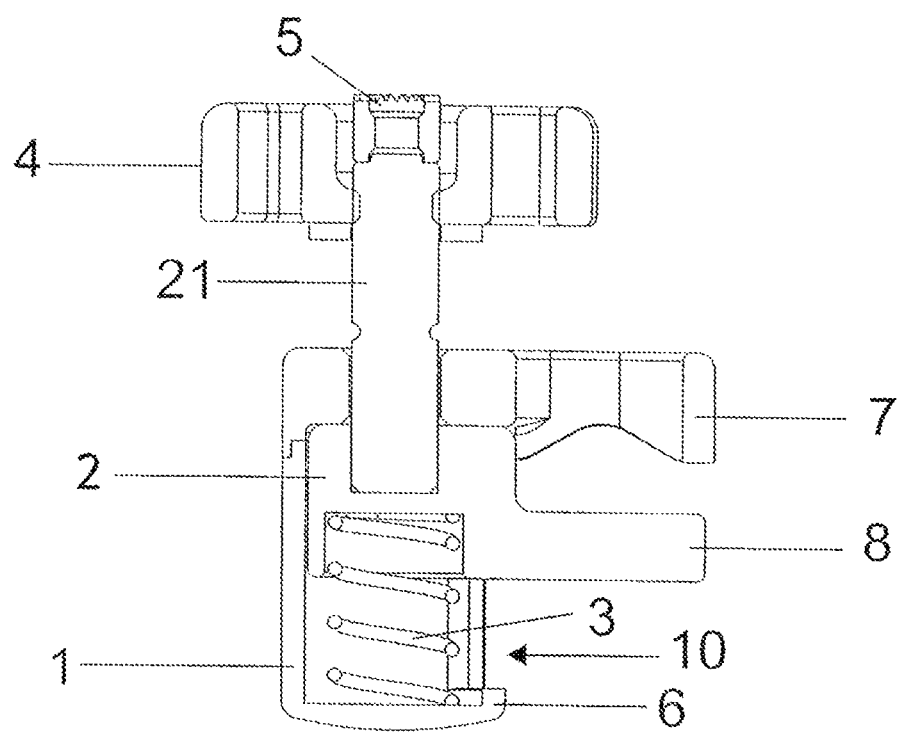
FIG. 7 shows a cross-section of the second embodiment according to the invention.

FIG. 7 shows a second example of an embodiment of an adapter according to the invention having, like in the case of the first embodiment, a first holding element 1 and a second holding element 2, moveably disposed within the first holding element 1, and a spring 3. In this example of an embodiment, the receiving state for a medical technical device is, like in the case of the examples of embodiments in FIG. 2 to FIG. 5, attained by a force acting against the restoring force of the spring 3. Regarding a detailed description of the receiving state reference is made to the aforementioned figures.

By a force acting against the restoring force of the spring 3, the distance between the first clamping element 7 and the second clamping element 8 is increased, and a receiving state is thereby attained. After insertion of the medical technical device, and in absence of a force acting counter to the direction of the restoring force of the spring 3, the tensioned spring 3 causes a movement of the second holding element 2 and, as a result, of the second clamping element 8 in a direction of the restoring force 3. A clamping state is thereby attained.

By rotating the second displacing element 4 in a clamping direction, the second holding element 2 (like in the description of FIG. 2 to FIG. 4) is displaced in a direction of the restoring force of the spring 3. A movement proof clamping state is thereby attained.

By a movement of the second displacing element 4 counter to the clamping direction, the movement proof clamping state is suspended, and removal of the medical technical device is at this stage possible. The removal may be simplified by, e.g., a force acting counter to the restoring force of the spring 3 once again and thus attaining the receiving state.

Figure 8:
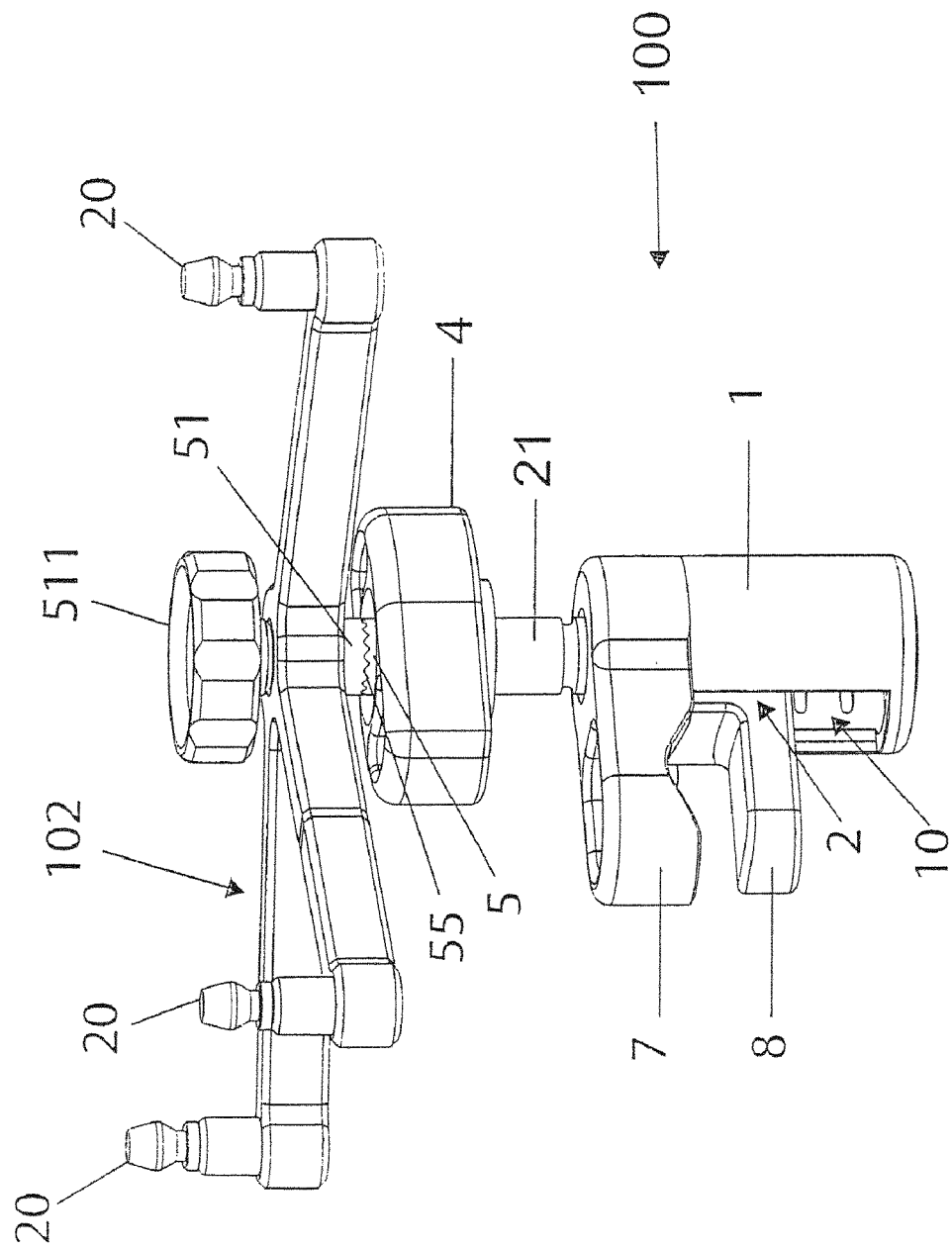
FIG. 8 shows the second embodiment of FIG. 7 with a position detecting system in a clamped state.

FIG. 8 shows an adapter according to the invention in a second embodiment with a position detecting system in the form of a tracker with three marker elements in a clamping state. Regarding the further descriptions, reference is made to the descriptions of FIG. 2 to FIG. 7

REFERENCE NUMERALS 1 first holding element
2 second holding element
3 spring
4 second displacing element
5 attachment element
6 bottom surface
7 first clamping element
8 second clamping element
10 receiving opening
11 first insertion opening
12 second insertion opening
20 marker element
21 first displacing element
51 attachment counter-element
55 structure elements
101 medical technical device
102 position detecting system
511 nut
F restoring force of spring
V clamping direction
U locking direction

What is claimed is:

1. An adapter for receiving a medical technical device and a position detecting system, comprising:
a first holding element;
a second holding element;
a spring exerting a restoring force on the second holding element; and
a fixing element for fixing the position detecting system;
wherein the first holding element has a receiving opening with a longitudinal extension direction, the receiving opening being configured to receive the second holding element within the first holding element, and the longitudinal extension direction of the receiving opening of the first holding element being parallel to the direction of the restoring force of the spring;
wherein the second holding element is movably supported in the first holding element and, by means of a force acting counter to the restoring force of the spring, is moveable in a direction counter to the restoring force of the spring such that the adapter is in a receiving state and the medical technical device is insertable into the adapter, wherein, in the absence of the force acting counter to the restoring force of the spring, the second holding element performs a movement in the direction of the restoring force by means of the restoring force of the spring and, as a result, the adapter is in a clamping state, in which the medical technical device inserted into the adapter is clamped between the first holding element and the second holding element; and
wherein the first holding element has a first clamping element, and the second holding element has a second clamping element, the second holding element, by a force acting counter to the restoring force of the spring, being moveable such that the distance between the first clamping element and the second clamping element increases and positions the adapter in the receiving state, wherein, in the absence of the force acting counter to the restoring force, the restoring force of the spring positions the adapter in the clamping state.

2. The adapter according to claim 1, wherein by a force acting counter to the restoring force of the spring, the clamping state of the adapter is reversible, and the medical technical device is removable from the adapter in this state.

3. The adapter according to claim 1, wherein the spring is connected to a bottom side of the second holding element.

4. An adapter for receiving a medical technical device and a position detecting system, comprising:
a first holding element;
a second holding element;
a spring exerting a restoring force on the second holding element; and
a fixing element for fixing the position detecting system;
wherein the first holding element has a receiving opening with a longitudinal extension direction, the receiving opening being configured to receive the second holding element within the first holding element, and the longitudinal extension direction of the receiving opening of the first holding element being parallel to the direction of the restoring force of the spring;
wherein the second holding element is movably supported in the first holding element and, by means of a force acting counter to the restoring force of the spring, is moveable in a direction counter to the restoring force of the spring such that the adapter is in a receiving state and the medical technical device is insertable into the adapter, wherein, in the absence of the force acting counter to the restoring force of the spring, the second holding element performs a movement in the direction of the restoring force by means of the restoring force of the spring and, as a result, the adapter is in a clamping state, in which the medical technical device inserted into the adapter is clamped between the first holding element and the second holding element; and
wherein a first displacing element, disposed at the second holding element, has a thread on an outer face and is operatively connected to a second displacing element, having a receiving opening with a mating thread for receiving the first displacing element, such that, by a rotational movement of the second displacing element in a clamping direction, the first displacing element and, therefore, the second displacing element are moveable in the direction of the restoring force of the spring, and, thereby, the adapter is in a movement proof clamping state.

5. The adapter according to claim 4, wherein the movement proof clamping state of the adapter is reversible by a rotational movement of the second displacing element counter to the clamping direction.

6. The adapter according to claim 4, wherein the first holding element has a first insertion opening for inserting the medical technical device, and the second holding element has a second insertion opening for inserting the medical technical device, the first insertion opening and the second insertion opening being configured to be transverse to the restoring force of the spring, and the first insertion opening and the second insertion opening completely passing through the first holding element and the second holding element, respectively, wherein the first insertion opening and the second insertion opening can be brought into congruence by a force acting counter to the restoring force of the spring and placing the adapter in the receiving state, and wherein, in the absence of the force acting counter to the restoring force, the restoring force of the spring places the adapter in the clamping state.

7. The adapter according to claim 4, wherein the first holding element has a first clamping element, and the second holding element has a second clamping element, the second holding element, by a force acting counter to the restoring force of the spring, being moveable such that the distance between the first clamping element and the second clamping element increases and placing the adapter in the receiving state, wherein, in the absence of the force acting counter to the restoring force, the restoring force of the spring places the adapter in the clamping state.

8. An adapter for receiving a medical technical device and a position detecting system, comprising:
a first holding element;
a second holding element;
a spring exerting a restoring force on the second holding element; and
a fixing element for fixing the position detecting system;
wherein the first holding element has a receiving opening with a longitudinal extension direction, the receiving opening being configured to receive the second holding element within the first holding element, and the longitudinal extension direction of the receiving opening of the first holding element being parallel to the direction of the restoring force of the spring;
wherein the second holding element is movably supported in the first holding element and, by means of a force acting counter to the restoring force of the spring, is moveable in a direction counter to the restoring force of the spring such that the adapter is in a receiving state and the medical technical device is insertable into the adapter, wherein, in the absence of the force acting counter to the restoring force of the spring, the second holding element performs a movement in the direction of the restoring force by means of the restoring force of the spring and, as a result, the adapter is in a clamping state, in which the medical technical device inserted into the adapter is clamped between the first holding element and the second holding element; and wherein the fixing element is immobilized on the second holding element, and the position detecting system has a fixing counter-element that is capable of engaging with the fixing element.

9. The adapter according to claim 8, wherein the fixing element has a cavity with a thread, and the fixing counter-element has a receiving opening with an identical thread, the cavity of the fixing element and the receiving opening of the fixing counter-element being directed in the direction of the restoring force of the spring and being configured such that, by means of a screw and a nut, a locking state of the position detecting system with the adapter is attainable by a force-fitting connection of the fixing element, the fixing counter-element, the screw, and the nut by means of a rotational movement of the nut in a locking direction.

10. The adapter according to claim 8, wherein the fixing element and fixing counter-element have on their mutual contact surfaces structures engaging with one another, and especially tooth structures engaging with one another, such that in the locking state a form-fitting and force-fitting locking of the position detecting system with the adapter is attained.

11. The adapter according to claim 8, wherein in a non-locking state the position detecting system is rotatably supported, and, as a result, the spatial orientation of the position detecting system is settable.

12. The adapter according to claim 11, wherein the spatial disposition of the position detecting system is settable in an angle determined by the size of the structure elements of the fixing element and the fixing counter-element.

13. The adapter according to claim 8, wherein the first holding element has a first insertion opening for inserting the medical technical device, and the second holding element has a second insertion opening for inserting the medical technical device, the first insertion opening and the second insertion opening being configured to be transverse to the restoring force of the spring, and the first insertion opening and the second insertion opening completely passing through the first holding element and the second holding element, respectively, wherein the first insertion opening and the second insertion opening can be brought into congruence by a force acting counter to the restoring force of the spring and placing the adapter in the receiving state, and wherein, in the absence of the force acting counter to the restoring force, the restoring force of the spring places the adapter in the clamping state.

14. The adapter according to claim 8, wherein the first holding element has a first clamping element, and the second holding element has a second clamping element, the second holding element, by a force acting counter to the restoring force of the spring, being moveable such that the distance between the first clamping element and the second clamping element increases and places the adapter in the receiving state, wherein in the absence of the force acting counter to the restoring force, the restoring force of the spring places the adapter in the clamping state.

* * * * *